US011033573B1

(12) United States Patent
Joy et al.

(10) Patent No.: US 11,033,573 B1
(45) Date of Patent: Jun. 15, 2021

(54) NON-IONIC COACERVATES FOR DRY, HUMID AND WET ADHESION

(71) Applicants: Abraham Joy, Copley, OH (US); Amal Narayanan, Cuyahoga Falls, OH (US)

(72) Inventors: Abraham Joy, Copley, OH (US); Amal Narayanan, Cuyahoga Falls, OH (US)

(73) Assignee: The University of Akron, Akron, OH (US)

( * ) Notice: Subject to any disclaimer, the term of this patent is extended or adjusted under 35 U.S.C. 154(b) by 0 days.

(21) Appl. No.: 16/700,130

(22) Filed: Dec. 2, 2019

Related U.S. Application Data

(60) Provisional application No. 62/800,069, filed on Feb. 1, 2019.

(51) Int. Cl.
| | | |
|---|---|---|
| *C08G 63/685* | (2006.01) | |
| *A61L 27/18* | (2006.01) | |
| *A61L 27/54* | (2006.01) | |
| *C08G 18/60* | (2006.01) | |
| *A61K 31/785* | (2006.01) | |
| *C09J 167/02* | (2006.01) | |

(52) U.S. Cl.
CPC ........ *A61K 31/785* (2013.01); *C08G 63/6856* (2013.01); *C09J 167/02* (2013.01)

(58) Field of Classification Search
CPC ............... A61L 27/18; A61L 2300/404; A61L 2300/412; A61L 2300/43; A61L 2300/602; A61L 2430/02; A61L 27/54; C08L 67/00; C08L 75/04; C08G 18/603; C08G 63/685; C08G 63/6856; C08G 69/44; C08G 73/0233; C08G 63/916; C08G 18/3275; C08G 18/3825; C08G 18/73; C08G 63/91; C09B 69/10
See application file for complete search history.

(56) References Cited

U.S. PATENT DOCUMENTS

| | | | |
|---|---|---|---|
| 8,673,986 | B2 | 3/2014 | Cha et al. |
| 9,272,069 | B2 | 3/2016 | Stewart et al. |
| 9,593,201 | B2 | 3/2017 | Joy et al. |
| 10,336,923 | B2 | 7/2019 | Joy et al. |
| 2017/0081568 | A1* | 3/2017 | Joy .......................... A61L 15/58 |
| 2018/0371158 | A1* | 12/2018 | Joy .......................... A61L 27/18 |

OTHER PUBLICATIONS

Swanson et al. (Polym. Chem. 2017, 8, 7195-7206) (Year: 2017).*
F. W. Tiebackx, Zeitschrift für Chemie und Ind. der Kolloide 1911, 8, 198-201.
R. Kausik, A. Srivastava, P. A. Korevaar, G. Stucky, J. H. Waite, S. Han, Macromolecules 2009, 42, 7404-7412.
D. S. Hwang, H. Zeng, A. Srivastava, D. V. Krogstad, M. Tirrell, J. N. Israelachvili, J. H. Waite, Soft Matter 2010, 6, 3232-3236.
E. Spruijt, J. Sprakel, M. A. Cohen Stuart, J. Van Der Gucht, Soft Matter 2009, 6, 172-178.
S. Lim, Y. S. Choi, D. G. Kang, Y. H. Song, H. J. Cha, Biomaterials 2010, 31, 3715-3722.
R. J. Stewart, J. Exp. Biol. 2004, 207, 4727-4734.
W. Wei, Y. Tan, N. R. Martinez Rodriguez, J. Yu, J. N. Israelachvili, J. H. Waite, Acta Biomater. 2014, 10, 1663-1670.
S. Kim, J. Huang, Y. Lee, S. Dutta, H. Y. Yoo, Y. M. Jung, Y. Jho, H. Zeng, D. S. Hwang, Proc. Natl. Acad. Sci. 2016, 113, E847-E853.
H. Shao, K. N. Bachus, R. J. Stewart, Macromol. Biosci. 2009, 9, 464-471.
H. Shao, R. J. Stewart, Adv. Mater. 2010, 22, 729-733.
S. Kaur, G. M. Weerasekare, R. J. Stewart, ACS Appl. Mater. Interfaces 2011, 3, 941-944.
L. Zhang, V. Lipik, A. Miserez, J. Mater. Chem. B 2016, 4, 1544-1556.
E. Kizilay, A. B. Kayitmazer, P. L. Dubin, Adv. Colloid Interface Sci. 2011, 167, 24-37.
D. Fischer, Y. Li, B. Ahlemeyer, J. Krieglstein, T. Kissel, Biomaterials 2003, 24, 1121-1131.
S. Seo, S. Das, P. J. Zalicki, R. Mirshafian, C. D. Eisenbach, J. N. Israelachvili, J. H. Waite, B. K. Ahn, J. Am. Chem. Soc. 2015, 137, 9214-9217.
J. P. Swanson, M. A. Cruz, L. R. Monteleone, M. R. Martinez, P. J. Costanzo, A. Joy, Polym. Chem. 2017, 8, 7195-7206.
J. P. Swanson, L. R. Monteleone, F. Haso, P. J. Costanzo, T. Liu, A. Joy, Macromolecules 2015, 48, 3834-3842.
J. P. Swanson, M. R. Martinez, M. A. Cruz, S. G. Mankoci, P. J. Costanzo, A. Joy, Polym. Chem. 2016, 7, 4693-4702.
D. W. Urry, B. Starcher, S. M. Partridge, Nature 1969, 222, 795-796.
S. Gokhale, Y. Xu, A. Joy, Biomacromolecules 2013, 14, 2489-2493.
H. Lee, N. F. Scherer, P. B. Messersmith, Proc. Natl. Acad. Sci. 2006, 103, 12999-13003.
J. Yu, Y. Kan, M. Rapp, E. Danner, W. Wei, S. Das, D. R. Miller, Y. Chen, J. H. Waite, J. N. Israelachvili, Proc. Natl. Acad. Sci. 2013, 110, 15680-15685.
S. Kaur, A. Narayanan, S. Dalvi, Q. Liu, A. Joy, A. Dhinojwala, ACS Cent. Sci. 2018, 4, 1420-1429.
Y. Xu, Q. Liu, A. Narayanan, D. Jain, A. Dhinojwala, A. Joy, Adv. Mater. Interfaces 2017, 4, DOI 10.1002/admi.201700506.
C. E. Stauffer, J. Phys. Chem. 1965, 69, 1933-1938.
S. Lim, D. Moon, H. J. Kim, J. H. Seo, I. S. Kang, H. J. Cha, Langmuir 2014, 30, 1108-1115.
K. Y. Huang, H. Y. Yoo, Y. Jho, S. Han, D. S. Hwang, ACS Nano 2016, 10, 5051-5062.
M. W. Liberatore, N. B. Wyatt, M. Henry, P. L. Dubin, E. Foun, Langmuir 2009, 25, 13376-13383.
F. Weinbreck, R. H. W. Wientjes, H. Nieuwenhuijse, G. W. Robijn, C. G. de Kruif, J. Rheol. (N. Y. N. Y). 2004, 48, 1215-1228.

* cited by examiner

*Primary Examiner* — Anna R Falkowitz

(74) *Attorney, Agent, or Firm* — Renner, Kenner, Greive, Bobak, Taylor & Weber

(57) ABSTRACT

A non-ionic polymer coacervate is provided that is useful for forming adhesive bonds between wet surfaces, and that operates over a wide range of pH.

15 Claims, 9 Drawing Sheets

(9 of 9 Drawing Sheet(s) Filed in Color)

NON-IONIC COACERVATES FOR DRY, HUMID AND WET ADHESION

CROSS-REFERENCE TO RELATED APPLICATION

This application claims priority from U.S. provisional patent application Ser. No. 62/800,069 filed on Feb. 1, 2018, which is incorporated herein by reference in its entirety.

STATEMENT REGARDING FEDERALLY SPONSORED RESEARCH OF DEVELOPMENT

This invention was made with government support under award number DMR 1352485 awarded by the National Science Foundation. The government has certain rights in the invention.

FIELD OF THE INVENTION

One or more embodiments of the invention provide non-ionic, self-coacervating polyesters that demonstrate rapid, water-tolerant crosslinking, resulting in strong underwater adhesion.

BACKGROUND OF THE INVENTION

Coacervation is the macroscopic phase separation of a solution to form two distinct fluid-fluid phases, namely, dilute and dense. The dense phase of the coacervate has unique characteristics such as high density, low viscosity, and low interfacial tension. Nature has employed protein coacervates as a means to overcome the challenge of adhesion between interfaces in a wet environment. For example, the low interfacial tension and low viscosity of the dense phase allow it to spontaneously prime rough underwater surfaces. Aquatic life forms such as sandcastle worms and mussels employ coacervation for efficient delivery of protein-rich adhesives in water resulting in robust underwater adhesion. For example, sandcastle worms secrete a mixture of oppositely charged proteins, forming a thermodynamically stable dense complex coacervate phase in the presence of metal salts at neutral pH. This complex coacervate is delivered to surfaces for initiating interfacial adhesion and the corresponding cohesive strength of the adhesive is obtained through enzymatic and mineral-mediated crosslinking reactions. Inspired by the sandcastle worm adhesive, multi-component complex coacervates formed from recombinant proteins and synthetic polymers have been used to create adhesive joints. The formation of complex coacervates with consistent physical properties requires careful tuning of the molar ratios of oppositely charged polymers, maintaining the correct pH and ionic strength, and temperature. This reduces the stability of complex coacervates to variations in pH and ionic strength. The instability to external factors and potential cytotoxicity of charged polymers can hinder the use of multicomponent complex coacervates in dynamic wet environments and on biological surfaces.

Recently, W. Wei, Y. Tan, N. R. Martinez Rodriguez, J. Yu, J. N. Israelachvili, J. H. Waite, "A Mussel-Derived One Component Adhesive Coacervate", *Acta Biomater.* 2014, 10, 1663-1670, incorporated herein by reference, demonstrated that one of the adhesive primer proteins (Mfp-3s) secreted by mussels undergoes coacervation. The coacervation behavior displayed by the Mfp-3s is distinct from the sandcastle worm adhesives since Mfp-3s undergoes one component self-coacervation from pH 3-6 and monovalent ionic strength ~100-600 mM. S. Seo, S. Das, P. J. Zalicki, R. Mirshafian, C. D. Eisenbach, J. N. Israelachvili, J. H. Waite, B. K. Ahn, "Microphase Behavior and Enhanced Wet-Cohesion of Synthetic Copolyampholytes Inspired by a Mussel Foot Protein", *J. Am. Chem. Soc.* 2015, 137, 9214-9217, incorporated herein by reference, translated the self-coacervation of Mfp-3s to synthetic polymers using designer copolyampholytes with strong cohesive interactions in wet conditions. However, these Mfp-3s-inspired copolyampholytes show coacervation only in narrow ranges of pH (4-5) and ionic strength (<20 mM) due to the strong columbic nature of self-association.

U.S. Pat. No. 8,673,986, incorporated herein by reference, describes a coacervate having an ionic polymer mixed with the adhesive protein of a mussel or of a species of the variome thereof. U.S. Pat. No. 9,272,069, incorporated herein by reference, describes adhesive complex coacervates composed of a mixture of one or more polycations, one or more polyanions, and one or more multivalent cations. What has been conspicuously absent is the demonstration of 'charge-free' coacervate adhesives that can self-coacervate in all ranges of pH and ionic strength. Such non-ionic, single component coacervates have significant advantages over the charged coacervates since their formation does not require optimization of the molar ratio of two or more components. Also, their increased stability to changes in external conditions allows the use of 'charge-free' coacervates in applications where the interfacial pH and ionic strength are susceptible to fluctuations, such as ruptured vascularized organs. There is an unmet need for non-ionic coacervates with strong underwater adhesion.

SUMMARY OF THE INVENTION

One or more embodiments of the present invention provide a non-ionic polymer coacervate that is useful for forming adhesive bonds between wet surfaces, and that operates over a wide range of pH. The non-ionic coacervate polymers are useful in biomedical situations where tissues need to be adhered or where implants or sensors need to be attached to tissues or skin surfaces. In addition, the non-ionic coacervate polymer adhesives may be used for engineering applications such as in automotive sensors, underwater sensors, and building structures. Also, the non-ionic coacervate polymers are useful for therapeutic (small molecule, macromolecule, protein, peptide, cells) delivery, as coatings for wet or moist surfaces, and for filling or accessing cracks and crevices underwater or in wet of moist environments.

For purposes of this specification, the term "wet" should be interpreted to include slightly wet, moist, damp, and humid.

One or more embodiments of the present invention provide non-ionic polymer coacervate represented by Formula I:

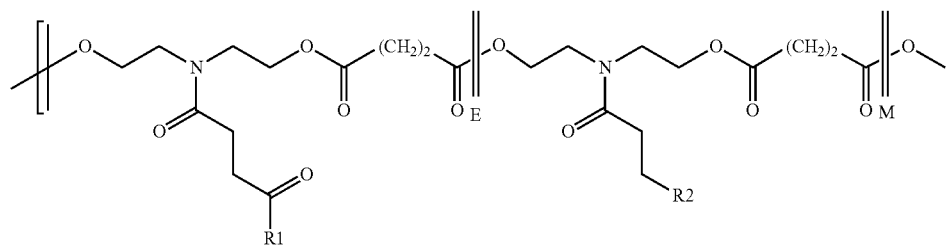

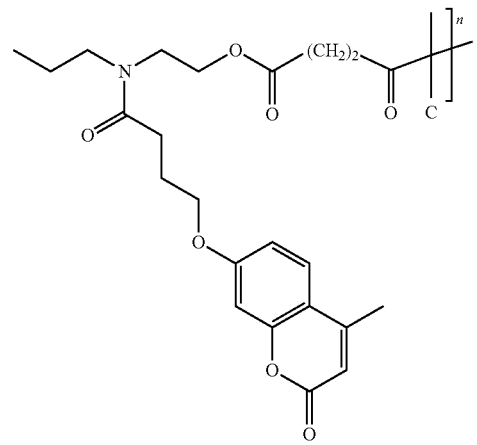

where R1 is selected from moieties that include an N- or N,N-substituted secondary or tertiary amide, R2 is selected from aliphatic groups, unsubstituted aromatic functional groups, and aromatic groups functionalized with one or more hydroxyl groups, n is from about 10 to about 500, E is from about 60 to about 95, M is from 0 to about 40, C is from about 5 to about 40, and where the sum of M+E+C is 100.

One or more embodiments of the present invention further provide a coacervate adhesive composition comprising a polymer having the formula

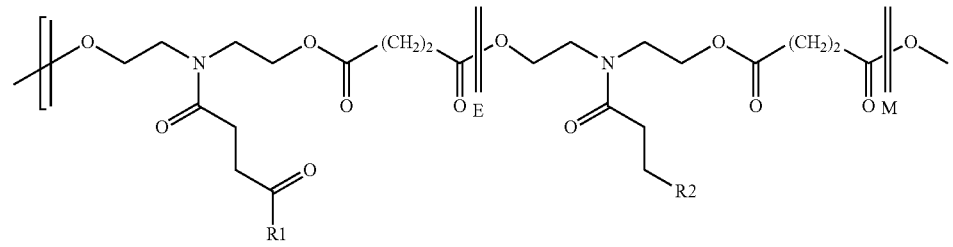

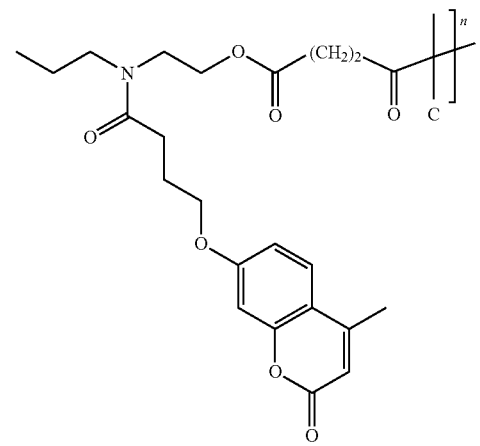

where R1 is selected from moieties that include an N- or N,N-substituted secondary or tertiary amide, R2 is selected from aliphatic groups, unsubstituted aromatic functional groups, and aromatic groups functionalized with one or more hydroxyl groups, n is from about 10 to about 500, E is from about 60 to about 95, M is from 0 to about 40, C is from about 5 to about 40, and where the sum of M+E+C is 100.

One or more embodiments of the present invention further provide a method for adhering surfaces under wet conditions, the method comprising contacting the surfaces with an adhesive composition comprising a polymer represented by the formula

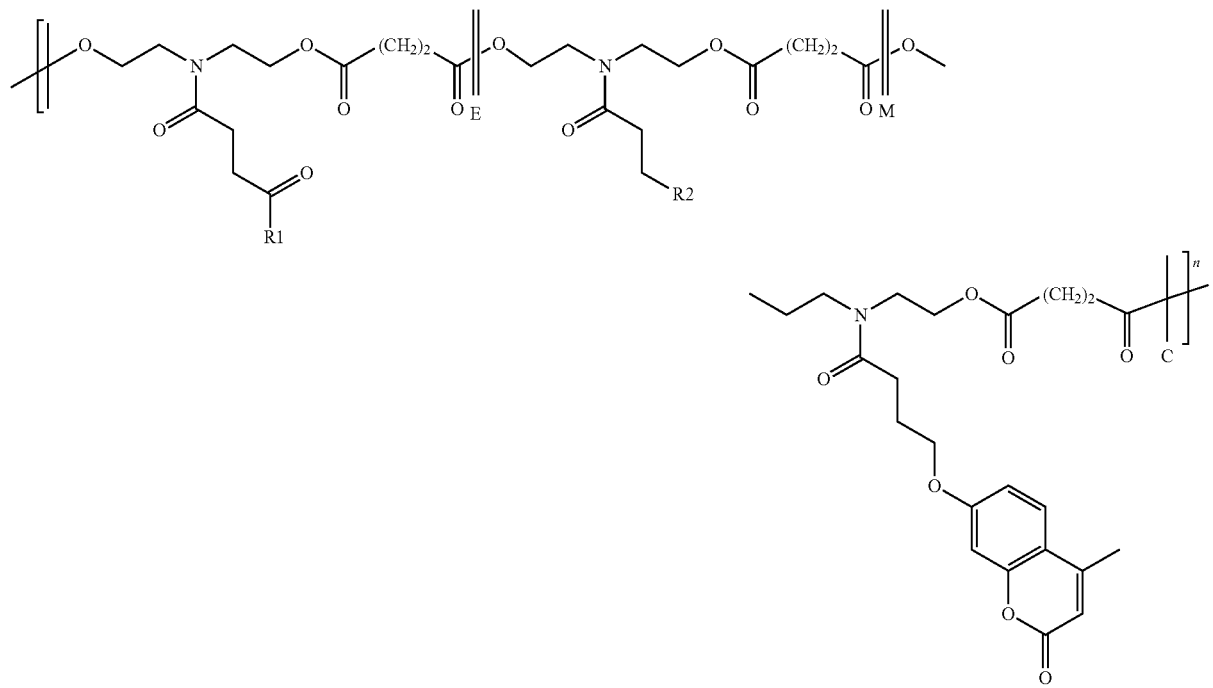

where R1 is selected from moieties that include an N- or N,N-substituted secondary or tertiary amide, R2 is selected from aliphatic groups, unsubstituted aromatic functional groups, and aromatic groups functionalized with one or more hydroxyl groups, n is from about 10 to about 500, E is from about 60 to about 95, M is from 0 to about 40, C is from about 5 to about 40, and where the sum of M+E+C is 100; and crosslinking the polymer to form an adhesive bond between the surfaces.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF ILLUSTRATIVE EMBODIMENTS

Figure 1:
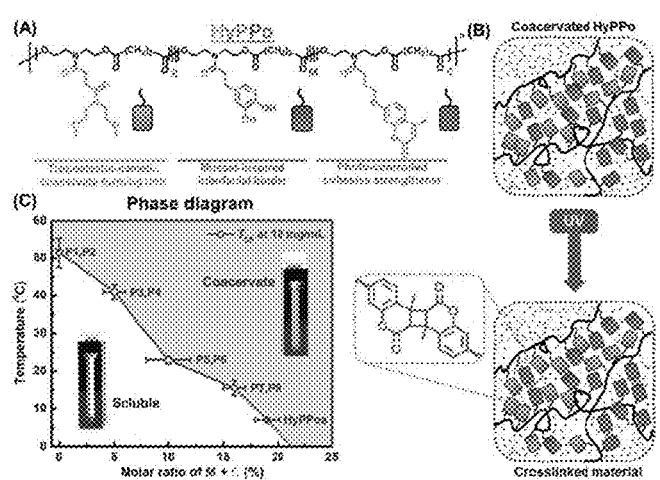
FIG. 1A is a schematic representation of a representative chemical structure of HyPPo.
FIG. 1B is a schematic representation of the [2+2] photocycloaddition reaction that modulates the cohesive strength of the HyPPo.
FIG. 1C is a phase diagram created using the cloud point temperature (TCP) of the copolyesters in DI water (concentration=10 mg/mL) with different molar ratios of M and C diol monomers. The details of the polyesters are described in Table 1.

One or more embodiments of this invention is based upon the discovery that certain thermoresponsive polyesters show 'tropoelastin-like' coacervation behavior. Tropoelastin, the soluble precursor to elastin, shows lower critical solution temperature (LCST) in aqueous medium, and above LCST the protein solution segregates into dilute and protein-rich dense phases. Similarly, these polyesters show hydrophobically-driven, single component coacervation. In one or more embodiments, polymers of the present invention are non-ionic, bioabsorbable, cell-compatible, and modular in nature, allowing incorporation of various functional groups. Advantageously, the polymers of the present invention provide significant advantages over any other reported coacervates.

In one or more embodiments, the present invention provides non-ionic, self-coacervating polyesters that demonstrate rapid, water-tolerant crosslinking, resulting in strong underwater adhesion. These non-ionic polyesters coacervate in most ranges of pH (acidic to basic) and ionic strength (0-1 M NaCl).

In one or more embodiments, the polymers of the present invention may be referred to as 'Hybrid Protein-like Polyester' (HyPPo) polymers, or coacervates. In one or more embodiments, the HyPPo polymers may be represented by Formula I:

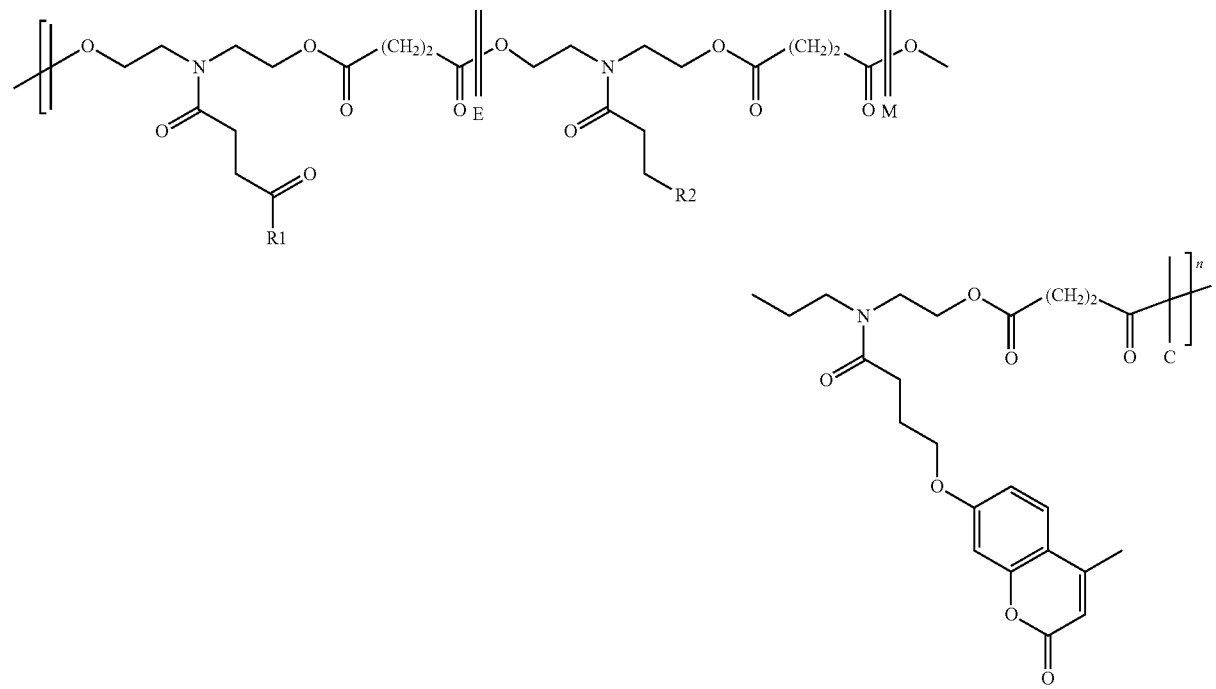

where R1 is selected from moieties that include an N- or N,N-substituted secondary or tertiary amide, R2 is selected from aliphatic groups, unsubstituted aromatic functional groups, and aromatic groups functionalized with one or more hydroxyl groups, n is from about 10 to about 500, E is from about 60 to about 95, M is from 0 to about 40, C is from about 5 to about 40, and where the sum of M+E+C is 100. In one or more embodiments, R1 is selected from 2-ethoxyethan-1-amine, Morpholine, bis(2-methoxyethyl)amine, and 2-methoxyethan-1-amine groups. In one or more embodiments, R2 is selected from methyl, benzene, phenol, catechol, resorcinol and pyrogallol groups. In one or more embodiments, the HyPPo polymers have an LCST in aqueous medium of from about −20 to about 100° C.

In one or more embodiments, the HyPPo polymers include a tropoelastin-mimetic domain (E), a mussel-inspired (M) domain that includes a catechol functional group, and a cross-linking (C) domain. Examples of HyPPo polymers may be represented by Formula II:

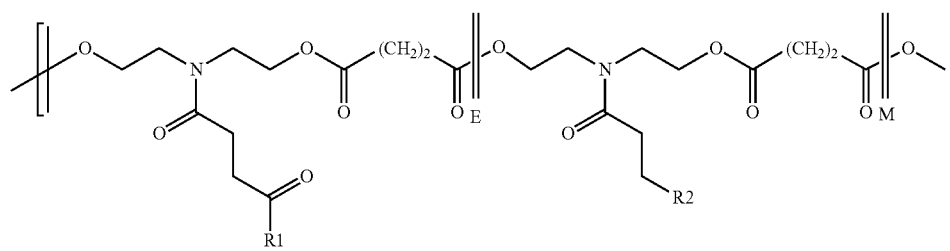

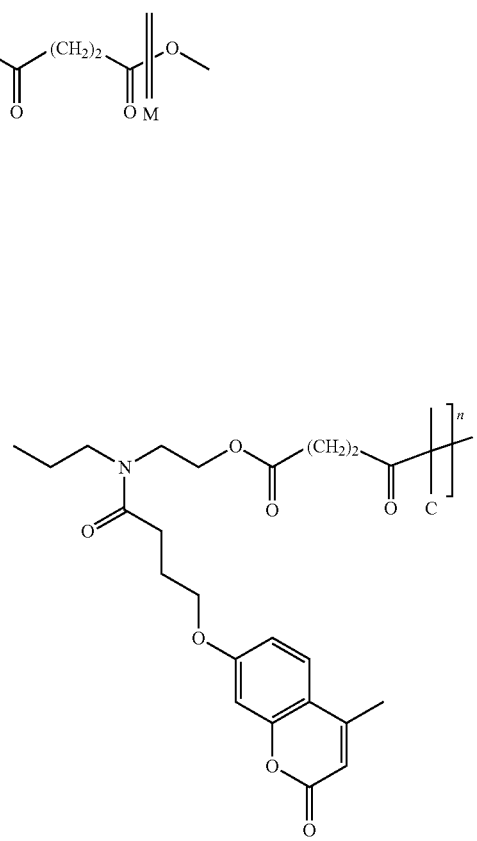

E = 60-95 mol %
M = 0-40 mol %
C = 5-40 mol %

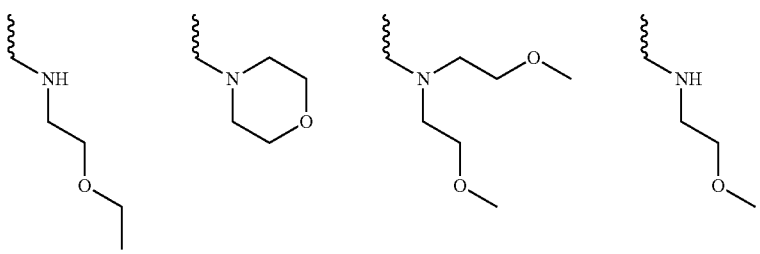

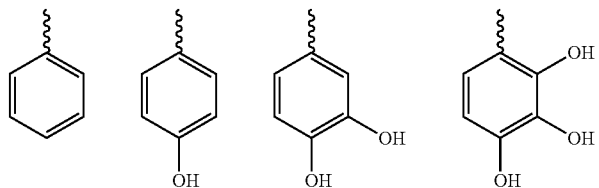

In one or more embodiments, HyPPo polymers comprise a class of statistical copolyesters that may be prepared from two or more N-functionalized diols, such as diethanolamides, and one or more diacid, such as succinic acid, and may be synthesized via polyesterification reactions. Synthesis procedures are further described in U.S. Pat. Nos. 9,593,201 and 10,336,923, both of which are incorporated herein by reference. An exemplary reaction scheme is shown in Scheme 1.

Scheme 1
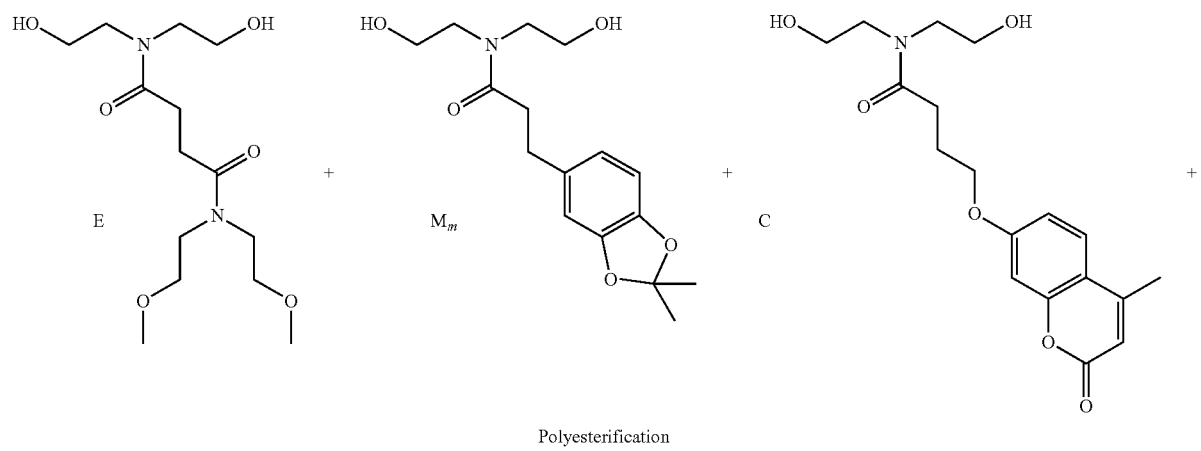
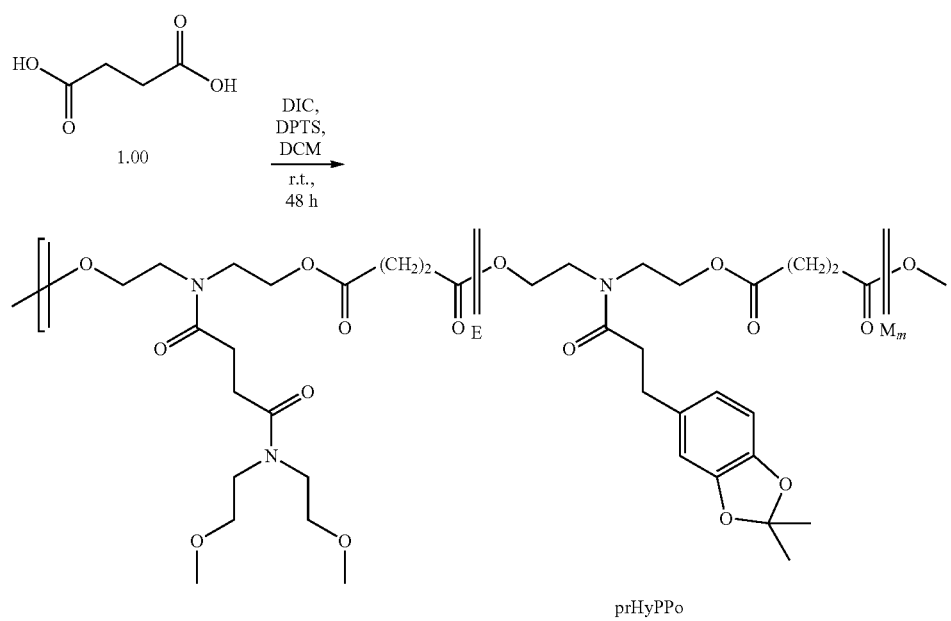
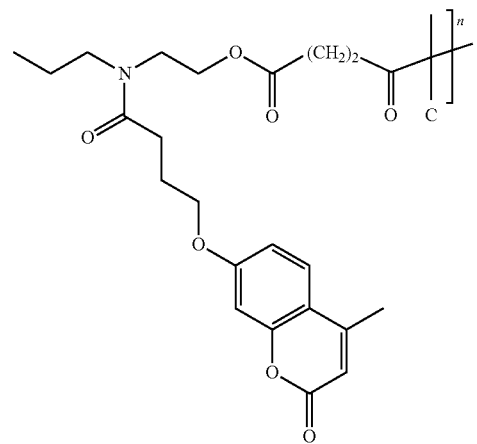

-continued
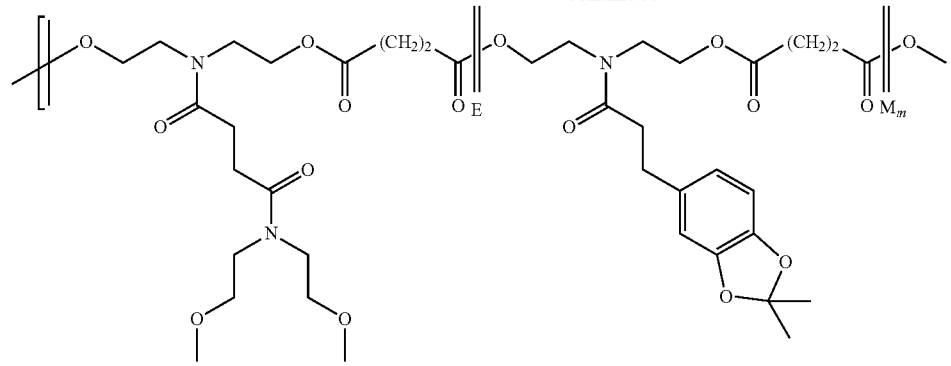
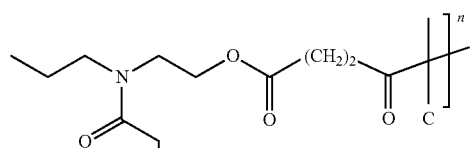
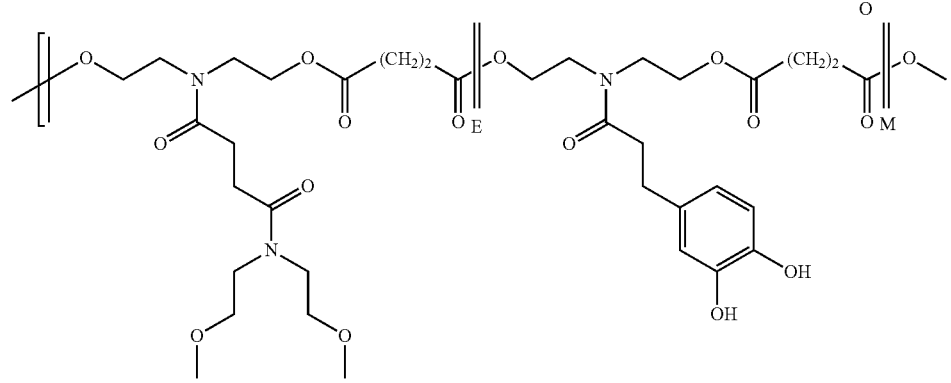
HyPPo
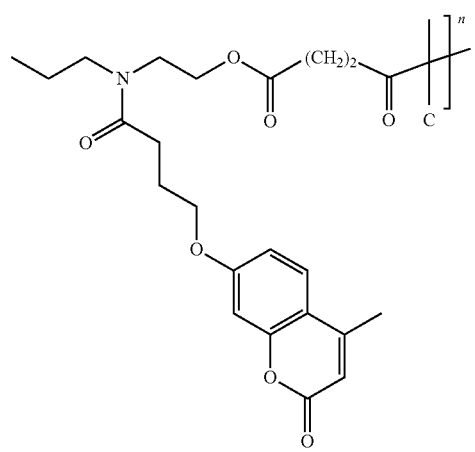
Deprotection of acetonide groups An example of a HyPPo polymer is shown in FIG. 1A.

In one or more embodiments, a first N-functionalized diethanolamide contains a tropoelastin-mimetic domain (E). Examples include bis(2-methoxyethyl)succinamide pendant monomer. Advantageously, bis(2-methoxyethyl)succinamide pendant monomer is characterized by a high LCST (~50° C.) for its homopolyester. In one or more embodiments, the addition of relatively hydrophobic diol monomers reduces the LCST to below room temperature. The polyesters containing an E domain show self-coacervation in aqueous medium at temperatures above the LCST.

In one or more embodiments, the polymer includes a second N-functionalized diethanolamide that includes one or more mussel-inspired (M) catechol functional groups. In one or more embodiments, the M group(s) enhance adhesion by interfacial and cohesive interactions.

In one or more embodiments, the HyPPo polymer also includes a crosslinking domain (C). In one or more embodiments, the crosslinking domain (C) is based on pendant coumarin groups. The crosslinking domain (C) facilitates the crosslinking of the HyPPo polymer. Crosslinking may be accomplished by any known manner. In one or more embodiments, coumarin groups may undergo [2+2] cycloaddition reaction when exposed to light (wavelength ~340-360 nm), providing instantaneous crosslinking and temporal control over the cohesive strength of the adhesive underwater (FIG. 1B).

In one or more embodiments, the HyPPo polymer is characterized by a molecular weight of from about 5 to about 200 kDa, in other embodiments, from about 5 to about 30, in other embodiments, from about 30 to about 70, in other embodiments, from about 70 to about 200 kDa.

Referring now to FIG. 1, a series of copolyesters was synthesized according to the parameters shown in Table 1, and the effect of M and C (0-20 mol %) on the cloud point temperature (TCP) was observed. FIG. 1C describes the phase diagram of copolyester aqueous solutions (concentration=10 mg/mL) with varying molar ratio of the M, C, and E at different temperatures. Due to the higher hydrophobicity of M and C, relative to E, the addition of M or C lowers the TCP. For this study, the copolyesters were designed to coacervate below room temperature (<22° C.), and near the freezing point of water, to improve their stability in a broad temperature range. FIG. 1C indicates that the incorporation of ~20 mol % of M and/or C provides copolyesters with TCP~7° C., which is ideal for creating adhesive coacervates for most real-life applications. In one or more embodiments, for high temperature applications, HyPPo can be made by increasing the ratio of E and reducing M or C and equilibrated in higher temperature above the LCST of resulting polymer.

TABLE 1

| Polymer | [a]E:M:C | $M_{n,GPC}$ (kDa) | [d]$T_{CP}$ (° C.) |
| --- | --- | --- | --- |
| P1 | 100:0:0 | 95.7[b] | 55 |
| P2 | 100:0:0 | 33.7[b] | 48 |
| P3 | 95:0:4 | 56.8[b] | 41 |
| P4 | 95:6:0 | 19.6[c] | 39 |
| P5 | 89:5:6 | 17.3[c] | 24 |
| P6 | 90:10:0 | 48.1[c] | 25 |
| P7 | 85:17:0 | 8.1[c] | 17 |
| P8 | 85:15:0 | 28.7[c] | 14 |
| HyPPo-20 | 80:20:0 | 22.1[c] | 7 |
| HyPPo-10 | 80:11:9 | 17.6[c] | 7 |

TABLE 1-continued

| Polymer | [a]E:M:C | $M_{n,GPC}$ (kDa) | [d]$T_{CP}$ (° C.) |
| --- | --- | --- | --- |
| HyPPo-15 | 80:6:14 | 13.5[c] | 1 |
| HyPPo-0 | 82:0:18 | 15.3[b] | 8 |

[a]Calculated using $^1$H NMR.
[b]Determined from the SEC traces or
[c]from the corresponding acetonide protected copolyesters.
$M_{n,GPC}$ of acetonide protected − 44 Da × no. of repeating unit of M.
[d]Quantified using temperature-dependent absorbance measurements at wavelength = 500 nm.

Table 2 summarizes four different copolyesters synthesized with ~20 mol % of M and/or C (HyPPo). The molar ratio of the diol monomers (E:M:C), number average molar mass (Mn), molar mass distribution (Đ), cloud point temperature (TCP), copolyester content in the coacervate dense phase (CDP), and interfacial tension of the coacervate dense phases in water (γ_DW) of the HyPPos was determined.

Figure 2:
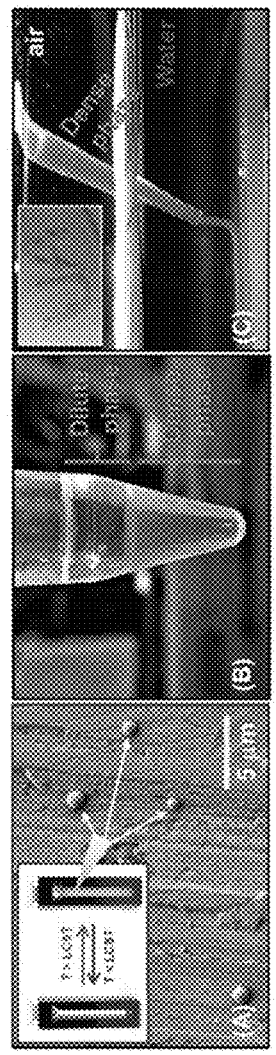
FIG. 2A is a scanning electron microscope (SEM) image of the photo-crosslinked (for stability) and dehydrated microdroplets formed at room temperature from 0.01 mg/mL solution of HyPPo-0 in DI water, captured at room temperature.
FIG. 2B is a SEM image of the macroscopic fluid-fluid phase separation displayed by 200 mg/mL solution of HyPPo-0 in DI water, captured at room temperature. The dilute phase (equilibrium solution) and dense phase (used for further studies) are indicated in the image.
FIG. 2C is a SEM image demonstration of the spreading of coacervate dense phase underwater (~1 nM rhodamine B is encapsulated for visibility), captured at room temperature.
Figure 3:
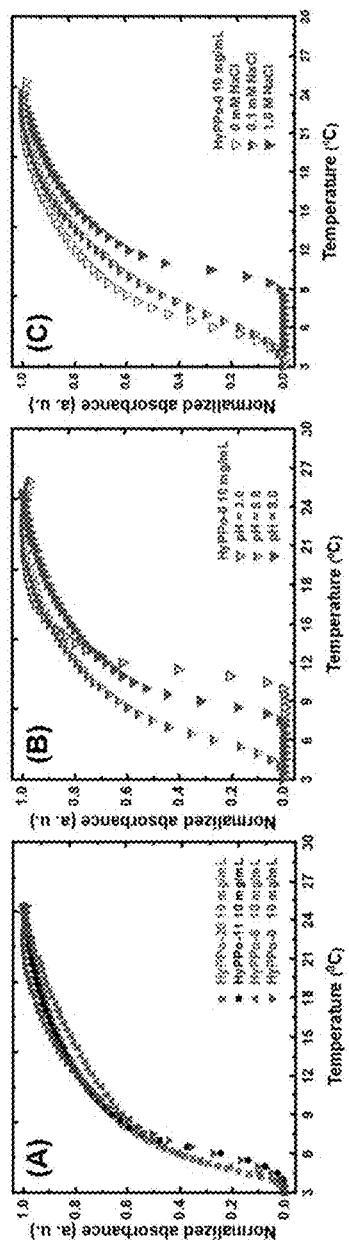
FIG. 3A is a representation of the temperature-dependent normalized absorbance of light at wavelength=500 nm by HyPP0-20, HyPPo-11, HyPPo-6, and HyPPo-0.
FIG. 3B is a representation of the temperature-dependent normalized absorbance of light at wavelength=500 nm by HyPPo-0 at pH=3.0, 6.8 and 9.0.
FIG. 3C is a representation of the temperature-dependent normalized absorbance of light at wavelength=500 nm by HyPPo-0 in 0 mM NaCl, 0.1 mM NaCl, 1.0 M NaCl.
Figure 4A:
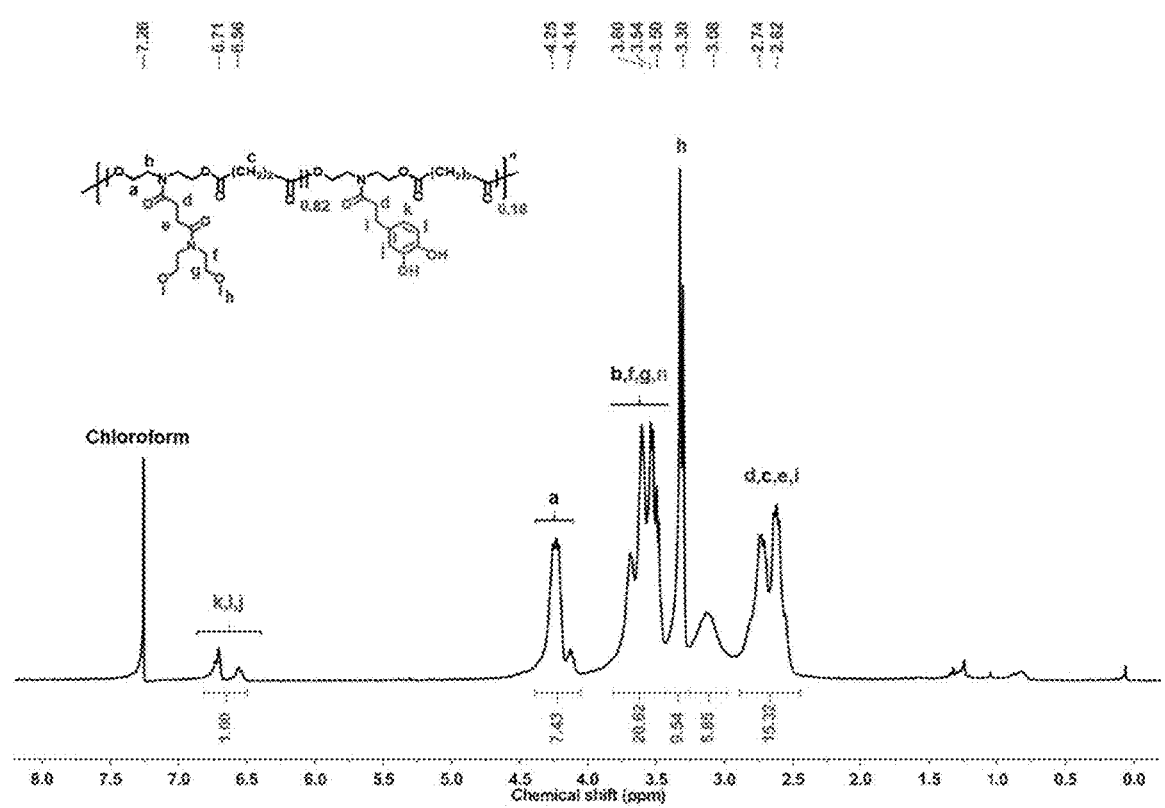
FIG. 4A is the $^1$H NMR spectra of the polyester HyPP0-20.
Figure 4B:
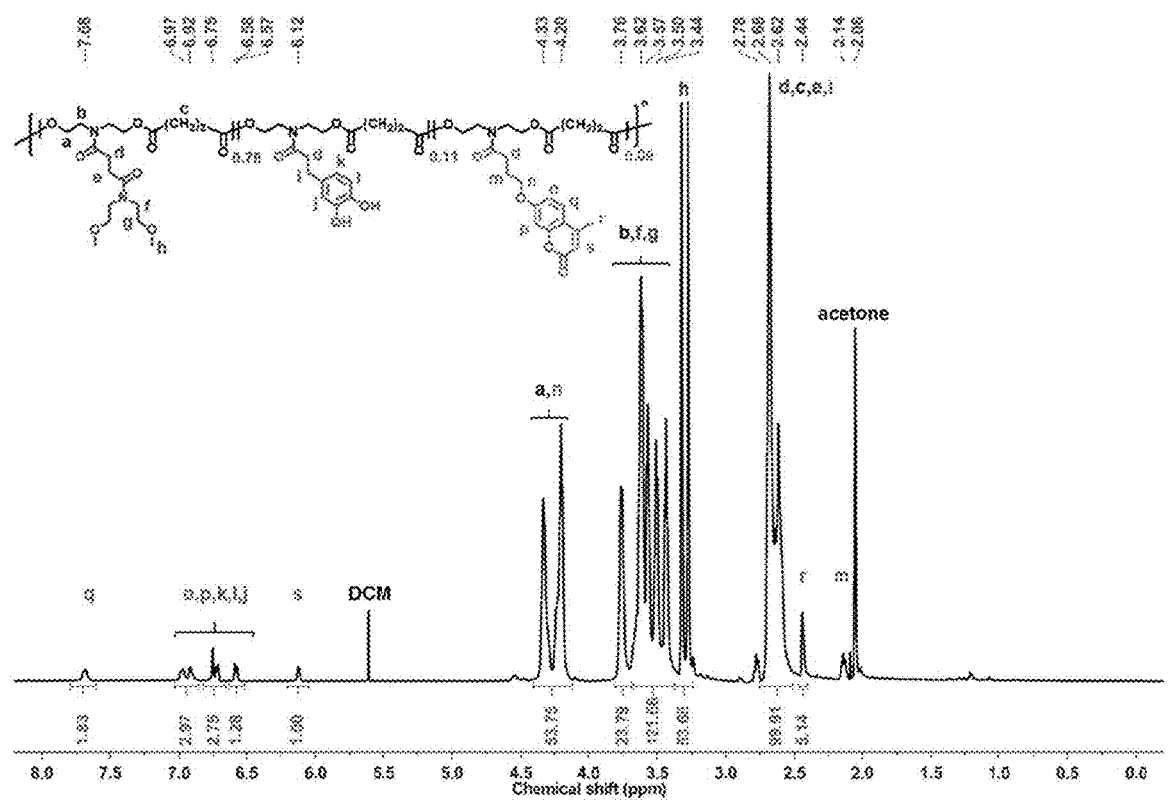
FIG. 4B is the $^1$H NMR spectra of the polyester HyPPo-11.
Figure 4C:
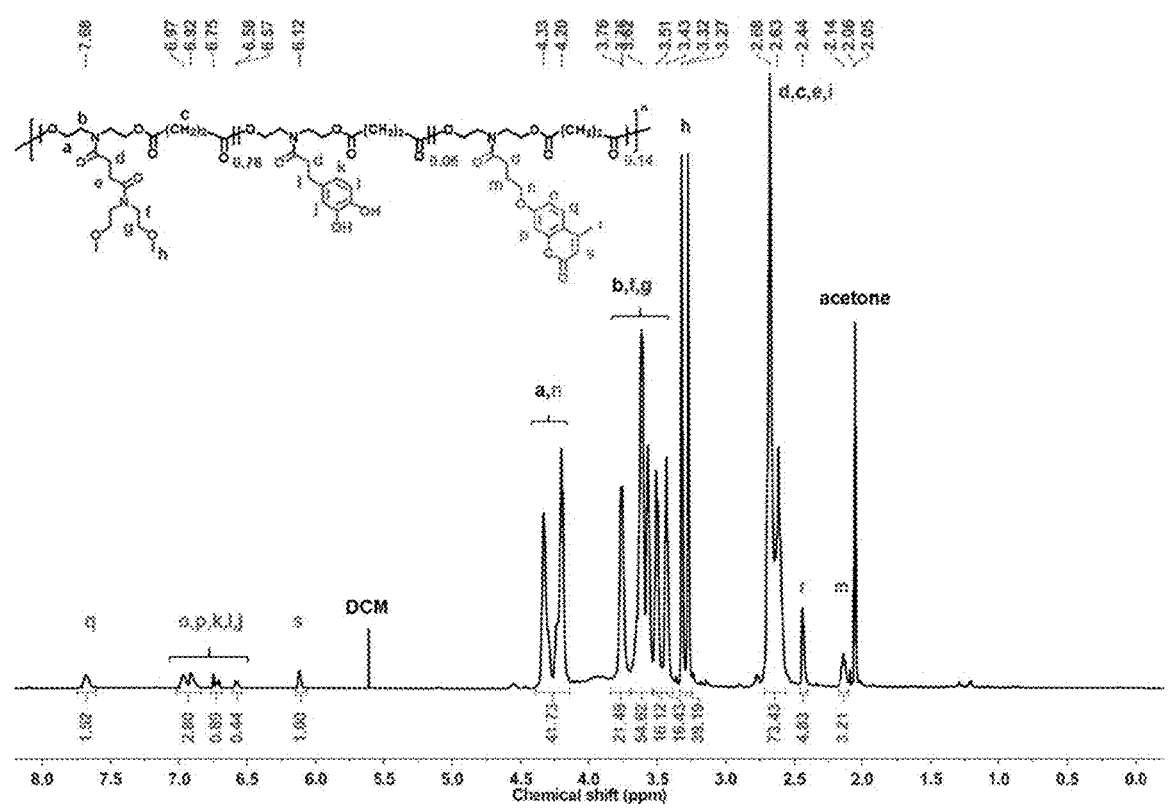
FIG. 4C is the $^1$H NMR spectra of the polyester HyPPo-6.
Figure 4D:
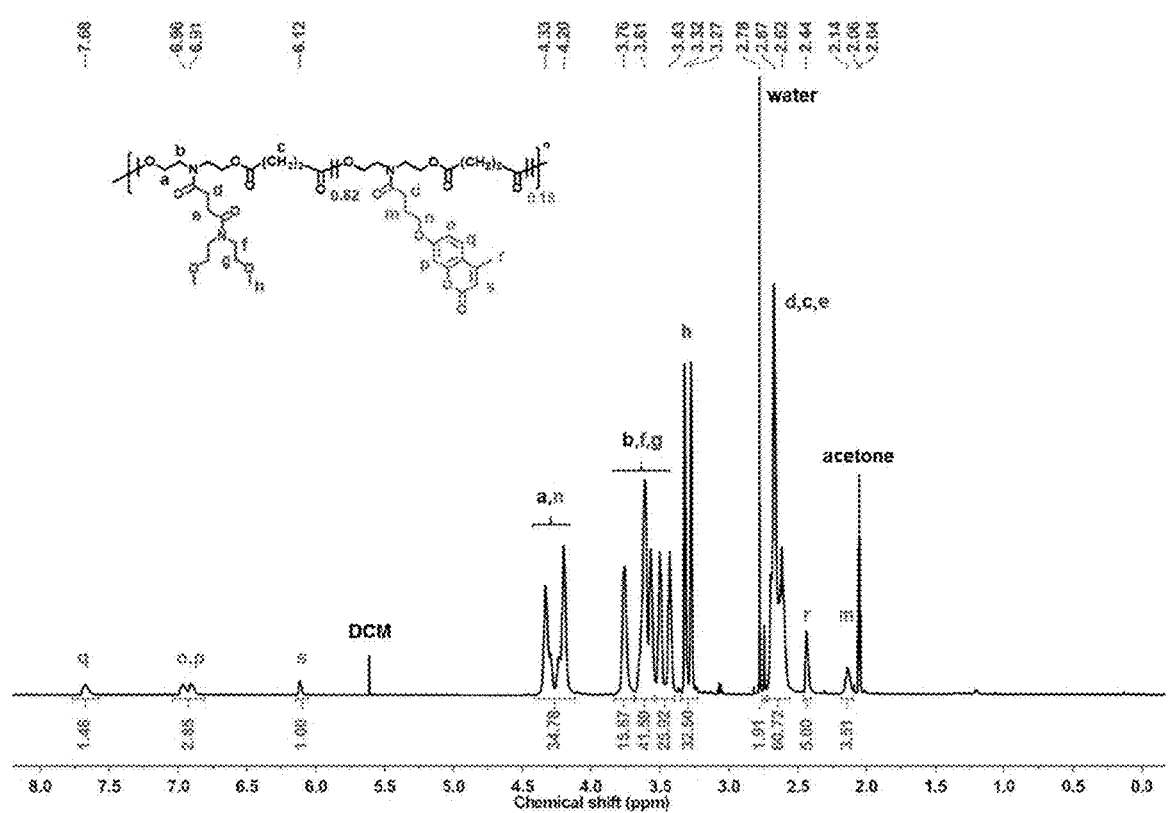
FIG. 4D is the $^1$H NMR spectra of the polyester HyPPo-0.

HyPPo polymers dissolve in water at temperatures of less than about 5° C. whereas at room temperature they may form kinetically evolving microdroplets (FIG. 2A). These microdroplets coalesce to form the macroscopic fluid-fluid phases, viz., dilute and dense (FIGS. 2B and C). The non-ionic nature of the coacervate association allows HyPPos to phase separate at room temperature in a wide range of pH (3-9; acidic to basic) and ionic strength (0-1 M NaCl) (FIG. 3C) as opposed to the ionic coacervates that only coacervate in a limited ranges of pH (mostly neutral) and ionic conditions. It should be noted from FIG. 3 that the TCP of HyPPo is affected by the changes in ionic strength and pH. However, in all tested experimental conditions, the TCP of HyPPos did not exceed room temperature and the formation of liquid and dense phases was observed.

TABLE 2

| Polyester | [a]E:M:C | [b]$M_n$ (kDa) | [b]Đ | [c]$T_{CP}$ (° C.) | [d]CDP (wt %) | [e]$\gamma_{DW}$ (mJ/m$^2$) |
| --- | --- | --- | --- | --- | --- | --- |
| HyPPo-20 | 80:20:0 | 22.1 | 1.8 | 6.8 | 48 | 0.16 ± 0.03 |
| HyPPo-11 | 80:11:9 | 11.6 | 1.7 | 7.2 | 50 | 0.13 ± 0.02 |
| HyPPo-6 | 80:6:14 | 17.5 | 1.6 | 7.0 | 46 | 0.13 ± 0.02 |
| HyPPo-0 | 82:0:18 | 15.3 | 1.5 | 7.5 | 45 | 0.20 ± 0.05 |

[a]The molar ratio of the diol monomers in the copolyesters calculated using $^1$H NMR (FIG. 4).
[b]Determined from the SEC traces of the corresponding acetonide protected copolyesters. $M_n$ = [($M_{n,GPC}$ of acetonide protected) − (44 Da × no. of repeating unit of M)].
[c]Quantified using temperature-dependent absorbance measurements at wavelength = 500 nm in DI water.
[d]Calculated from the gravimetric analysis.
[e]Determined using pendant drop tensiometer in DI water.

The dense phase of the coacervate is a binary mixture of copolyester and water that is in thermodynamic equilibrium with its coexisting dilute phase. The gravimetric analysis of the dense phases formed from HyPPos show ~50:50 (wt/wt %) ratio of bulk copolyester to water (Table 2, CDP). The interfacial tension of these dense phases in water (γ_DW) was measured using the pendant drop method (Table 2). The pendant drop shape was captured with a high-speed camera and interfacial tension of the dense phase was quantified using the Laplace equation. Compared to nearly any water-insoluble liquid, all the dense phases showed similar and extremely low interfacial tension underwater (~0.15 mJ/m2), which is a notable characteristic of coacervation. The dense phase is proposed to have a bicontinuous, nanometer-scale biphasic separation within the dense macrophase. One of the nanophases consists of 'bulk-like' water and the other is a 'polymer-rich' phase. This bicontinuous nature of the dense phase is proposed to be the origin of the distinct low interfacial tension observed for coacervates.

Figure 5:
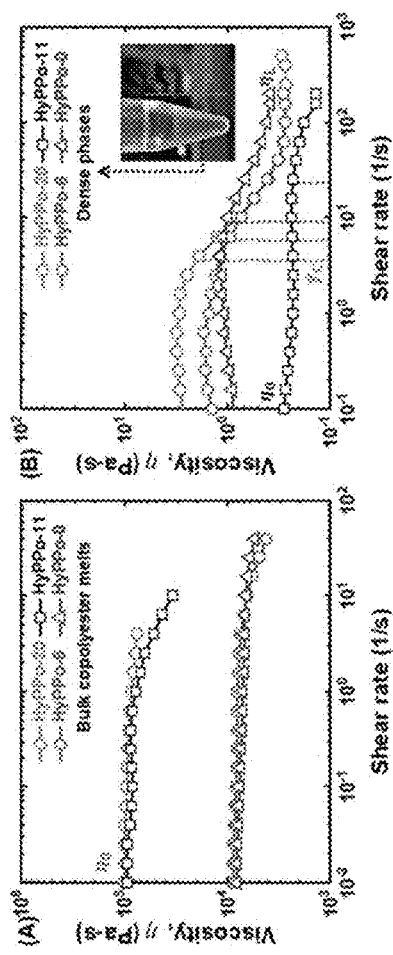
FIG. 5A is a graphical representation of the steady-state flow measurements of bulk HyPPo melts.
FIG. 5B is a graphical representation of the steady-state flow measurements of the coacervate dense phases corresponding to the bulk HyPPo melts of FIG. 5A, formed in DI water at 25° C.

The viscoelastic properties of the bulk copolyesters (HyPPos in their melt state) and their corresponding coacervate dense phases were analyzed using steady-state flow and small amplitude oscillatory shear (SAOS) measurements at 25° C. FIGS. 5A and B show the viscosity (q) response to shear rate ($\dot{\gamma}$) of the bulk copolyesters and the coacervate dense phases formed from 200 mg/mL aqueous solution of the corresponding bulk copolyesters, respectively. The zero-shear viscosity ($\eta\_0$, $\eta$ at low $\dot{\gamma}$) of the bulk HyPPo-20, HyPPo-11, HyPPo-6, and HyPPo-0 were found to be $1.0\times 10^5$, $9.5\times 10^4$, $8.8\times 10^3$, and $8.1\times 10^3$ Pa-s, respectively. The of the bulk polyesters remained relatively constant at $\dot{\gamma}$ between $10^{-2}$ to $10^1$ $s^{-1}$. The coacervate dense phases formed from HyPPo-20, HyPPo-11, HyPPo-6, and HyPPo-0 showed $\eta_0$~2.5, 0.3, 1.4, and 0.9 Pa-s, respectively (FIG. 5B). An abrupt shear thinning behavior was observed at $\dot{\gamma}(\dot{\gamma}C)$ of 4, 25, 7, and 10 $s^{-1}$ for HyPPo-20, HyPPo-11, HyPPo-6, and HyPPo-0, respectively. The shear thinning is an indication of the shear-induced structural changes in the material. When $\dot{\gamma}>\dot{\gamma}\_C$, we hypothesize that the dense macrophase might be restructuring along the plane of shear and causing the observed decrease in viscosity (FIG. 5B). This non-Newtonian behavior attains limiting and constant viscosity ($\eta_L$), which is observed from $\dot{\gamma}>25$, 40, 150, and 100 $s^{-1}$ till 200 $s^{-1}$ for HyPPo-20, HyPPo-11, HyPPo-6, and HyPPo-0, respectively.

Figure 6:
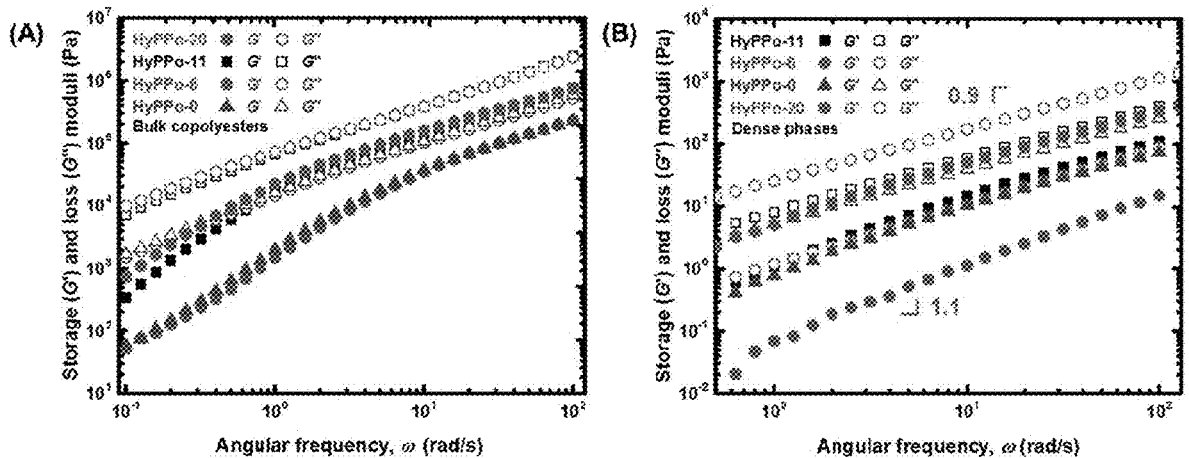
FIG. 6A is a graphical representation of the small amplitude oscillatory sweep response of the bulk HyPPos.
FIG. 6B is a graphical representation of the small amplitude oscillatory sweep response of thecoacervate dense phases corresponding to the bulk HyPPos of FIG. 6A, at 25° C.

SAOS measurements of the bulk copolyester melts show that the loss modulus (G")>storage modulus (G') at angular frequencies ($\omega$) between 0.1 to 100 rad/s, indicating the liquid-like behavior of the bulk copolyesters (FIG. 6A). FIG. 6B describes the response of the coacervate dense phases to $\omega$. A viscous behavior (G">G') was observed throughout the experimental regime and G" and G' scaled to $\sim\omega^{1.1}$ and $\sim\omega^{0.9}$, respectively between 0.1 to 100 rad/s. From the rheological measurements, it was found that $\eta_0$ and G" of the bulk copolyesters reduced by more than $10^3$ times when coacervated. The low viscosity and shear thinning behavior of these coacervates allow delivery of coacervates as continuous filaments without any mass loss. Observation shows the ease in delivering the HyPPo-O dense phase from a polypropylene (hydrophobic) micropipette tip without any resistance underwater. Density higher than water and the low interfacial tension allows immediate wetting of coacervates to hydrophilic surfaces submerged underwater.

The adhesive performances of the HyPPos on glass were quantified using lapshear and tack adhesion geometries underwater. From the force-distance curve (FIGS. 7A and 7C), the adhesion strength and the work of adhesion were calculated. The substrates adhered using HyPPo-20 and HyPPo-11 showed negligible adhesion strength and failed cohesively before testing. HyPPo-6 and HyPP-0 showed lapshear adhesion strength of 96±16 and 101±22 kPa, respectively. The lapshear work of adhesion was found to be 7.8±1.9, and 3.8±1.1 mJ for HyPPo-6 and HyPPo-0, respectively (FIG. 7B). In contrast to the lapshear strength measurements, the tack adhesion test was able to capture the adhesion behavior of HyPPo-11 (FIG. 7C). The tack adhesion strengths of HyPPo-11, HyPPo-6, and HyPPo-0 were quantified to be 7±3, 66±4, and 54±3 kPa, respectively (FIG. 7D). The tack work of adhesion measured from the unloading curve in the force-distance profiles were found to be $2\times 10^{-3}$, 0.21±0.06, and 0.09±0.02 mJ for HyPPo-11, HyPPo-6, and HyPPo-0, respectively (FIG. 7D).

Advantageously, the coacervate adhesives of the present invention are useful to create adhesive joints such as coating, bonding, curing, and testing in underwater conditions. Kaur et al., *ACS Appl. Mater. Interfaces* 2011, 3, 941-944, incorporated herein by reference, have developed complex coacervate formulations encapsulated with polyethylene glycol-diacrylate that are applied outside water, but cured and tested underwater, which show about 1 MPa lapshear adhesion strength for bonded aluminum substrates. Lim et al., *Biomaterials* 2010, 31, 3715-3722, incorporated herein by reference, performed all steps of adhesive joint fabrication underwater using complex coacervate made from association of recombinant Mfp and hyaluronic acid and obtained lapshear adhesion strength of about 200 kPa underwater.

However, since many prior coacervate adhesives studies rely on slow oxidative and free radical polymerization reactions for cohesive strength, they require extended curing time (about 24 h) for making robust lap-joints. In contrast, the rapid curing of HyPPos provides strong adhesive joints underwater.

In one or more embodiments, HyPPos polymers of the present invention cure within about 20 hours or less, in other embodiments, within about 10 hours or less, in other embodiments, within about 5 hours or less, in other embodiments, within about 1 hours or less, in other embodiments, within about 30 minutes or less, in other embodiments, within about 10 minutes or less. In one or more embodiments, HyPPos polymers of the present invention cure within about 3 minutes or less. The rapid crosslinking of the adhesive and degradability of HyPPos have broad significance for the use of these water-borne adhesives as surgical sealants or tissue adhesives.

During the adhesion measurements, both HyPPo-6 and HyPPo-O showed statistically similar lapshear adhesion strength and failed at the substrate-adhesive interface. However, the work of adhesion measured from both lapshear and tack geometries show the significantly higher performance of HyPPo-6 compared to HyPPo-0. This indicates that the catechol is playing a significant role in enhancing the work of adhesion of HyPPo-6.

Tack adhesion tests were performed of prHyPPo-6, wherein the hydroxyl groups of catechol in prHyPPo-6 are protected using the acetonide group (Scheme 1). From the tack adhesion measurements, the adhesion strength of prHyPPo-6 (56±6 kPa) was statistically indistinguishable to HyPPo-6, and the work of adhesion was significantly lower (0.07±0.01 mJ) than HyPPo-6. This reiterates the influence of hydroxyl groups in increasing the work of adhesion of the material. Previously, catechol has been shown to increase the interfacial and cohesive interactions of Mfp and synthetic polymers. The phenolic hydroxyl groups can form multimodal hydrogen bonding interactions with silica (glass) and enhance the adhesive-substrate interfacial interactions. Also, hydrogen bonds between hydroxyl groups and other polar molecules in the copolyester can increase the toughness (during tensile-type adhesion measurements, the work of adhesion c toughness) of HyPPo-6 compared to prHyPPo-6 and HyPPo-0. Since these adhesives have similar adhesion strength and failure occurs at the adhesive-substrate interface, it is proposed that the hydrogen bonds in the bulk of HyPPo-6 act as sacrificial interactions that dissipate the unloading force and results in the higher work of adhesion of HyPPo-6 compared to prHyPPo-6 and HyPPo-0.

In one or more embodiments, the non-ionic, single component coacervate adhesives (HyPPos) according to the present invention can coacervate in wide ranges of pH (3-9) and ionic strength (0-1 M NaCl). In one or more embodiments, the HyPPos displays low underwater interfacial tension, low viscosity, and shear thinning behavior, which allow facile and efficient delivery and uniform spreading of coacervates on surfaces submerged in water.

Advantageously, the polymers of the present invention are useful to coat and adhere to surfaces under wet conditions, including underwater. Thus, the present invention provides a method for adhering surfaces under wet conditions, the method comprising contacting the surfaces with an adhesive composition comprising a HyPPos polymer of the present invention, and crosslinking the polymer to form an adhesive bond between the surfaces. In one or more embodiments, the polymer may be spread, adhered, cured, and even tested under water, and exhibits excellent adhesion strength. In contrast to the complex coacervates, the 'charge-free' coacervate polymers of the present invention are useful as tissue adhesives and sealants, adhesives for sensor attachment to wet skin, and as sprayable adhesives. Advantageously, polymers of the present invention have enhanced stability to changes in external conditions, cytocompatibility, biodegradability, and are modular nature, capable of incorporating various functional groups and crosslinkers.

In order to demonstrate the practice of the present invention, the following examples have been prepared and tested. The examples should not, however, be viewed as limiting the scope of the invention. The claims will serve to define the invention.

EXAMPLES

Synthesis
  Polymerization

The polymerization of the N-functionalized diethanolamides were carried out in similar method as reported by Gokhale et al., *Biomacromolecules* 2013, 14, 2489-2493, incorporated herein by reference. As an example, the preparation of prHyPPo-11 is described in Scheme 1. To a 100 mL round bottom flask (r.b.) equipped with magnetic stir bar, added E (3.015 g, 9.82 mmol, 0.8 eq.), Mpr (380 mg, 1.23 mmol, 0.1 eq.), C (429 mg, 1.23 mmol, 0.1 eq.), and DPTS (1.445 g, 4.91 mmol, 0.4 eq.). The r.b. was then sealed with a rubber septum and connected to a Schlenk line. The reaction vessel was kept under vacuum for 10 min and back filled with dry N2. his cycle was repeated for three times. Under N2, anhydrous DCM (35 mL) was added to the r.b. and allowed to homogenize for 30 min. Then the r.b. was cooled down using an ice bath for 10 min prior to the dropwise addition of DIC (7.69 mL, 49.09 mmol, 4 eq.). The reaction mixture was stirred at room temperature for 48 h. After the completion of reaction, urea formed during the esterification reaction was filtered off and the crude was concentrated under reduced pressure. The concentrated reaction mixture was then dissolved in methanol (~20 mL) and transferred to a regenerated cellulose membrane dialysis bag (MWCO=3.5 kDa) and dialyzed against methanol for 72 h. The solvent was changed regularly during this time. The polymer solution was collected from the dialysis membrane and concentrated under reduced pressure and precipitated against diethyl ether (×2). The obtained polymer was then dried under high vacuum for overnight to obtain colorless polyesters. The polyesters were characterized using 1H NMR and GPC.

Deprotection of Acetonide Groups were Performed to Obtain HyPPos with Free Catechol Groups The acetonide protected polyesters were deprotected using similar methods as reported previously in the art. Typically, in a sealed two neck r.b. with one neck connected to an addition funnel, concentrated acetonide-protected polymer solution in anhydrous DCM (~2 g polymer in 1 mL DCM) was transferred under N2. To this set up, vacuum was applied to remove the solvents and air. After 15 min of vacuum, the reaction container was back filled with N2. The vacuum-nitrogen cycle was repeated for three times. Under N2 conditions, 20 mL of dry DCM was then transferred to the reaction vessel and allowed to homogenize for 10 min. After the homogenization, the r.b. was kept at −20° C. for 10 min prior to the slow dropwise addition of TFA (5.0 mL). After the complete addition of TFA, 0.2 mL of TIPS was added to the reaction mixture and the reaction was stirred at room temperature for 2 h under N2. After the predetermined time, the volatile compounds were removed under reduced pressure. The concentrated solution was dissolved in acetone and precipitated against diethyl ether (×3). The precipitate was then dried under high vacuum overnight to obtain colorless polyesters. The obtained polyesters were characterized using 1H NMR spectroscopy (FIG. 4 A-D).

Cloud Point Temperature Analysis

The cloud point temperature (TCP) of the polyesters in aqueous medium was determined using a Shimadzu UV-1800 UV-VIS spectrophotometer equipped with a Shimadzu S-1700 thermoelectric single cell holder in a 1 cm quartz cell with nitrogen chamber. The polyester solutions (10 mg/mL) were prepared in degassed Millipore water (unless noted) and kept at 3° C. overnight. This solution was transferred to a precooled quartz cuvette. The cuvette was kept at 3° C. in the cell holder with nitrogen flow till the absorbance was equilibriated. During the experiment, the temperature was raised from 3 to 30° C. at a rate of 1.0° C./min and the absorbance was recoded at wavelength $\lambda=500$ nm with reference to Millipore water. The temperature at which the normalized absorbance reach 50% was recorded as the $T_{CP}$.

Imaging the Nanodroplets

Scanning electron microscopy (SEM) was used to image the kinetically stable nanodroplets formed during the separation. A 0.01 mg/mL aqueous solution of HyPPo-O was cooled below its TCP and quickly casted on stainless steel SEM stubs pre-warmed using UV lamp. The solution was irradiated with light of wavelength ~320-420 nm and intensity at the substrate 300 mW/cm2 for 5 min. The sample was dried in ambient condition overnight and further dried under vacuum for 24 h. Prior to imaging the samples were sputter coated with gold for contrast.

Liquid-Liquid Phase Separation

The liquid-liquid phase separation (FIG. 3B) is a characteristic feature of coacervation. The dense phase for the experiments were separated in the following way. To a centrifuge tube with 2.0 g HyPPo added 10 mL of degassed Millipore water and kept at −4° C. for 30 min. The HyPPo-water mixture was taken out and thoroughly mixed at room temperature. With the melting of ice formed inside the centrifuge, HyPPo start dissolving. The freeze-melt cycle was repeated multiple times to achieve homogenous solution at temperature below TCP. The solution (200 mg/mL) was then kept at room temperature overnight for obtaining the dilute and dense phases.

Interfacial Tension Measurement Using Pendant Drop Method

We used pendant drop shape analysis to quantify the interfacial tension of the coacervate dense phases. The dense phases of the coacervate was transferred to a syringe and a drop was created underwater from 30-gauge steel needle. The drop shape analysis was performed using a Rame-hart drop shape analyzer. Young-Laplace equation was used to covert the drop shape to interfacial tension (γ_DW). Ten independent droplets of each polyester dense phases immersed in water were analyzed for 1 min after equilibration.

Rheology

The viscoelastic properties of the bulk HyPPos and their corresponding coacervate dense phases were studied using a TA ARES-G2 rheometer. For the bulk polyesters, 8.0 mm (diameter), 0.0872 rad cone plate was used at top. The viscous HyPPos were loaded to a preheated (~50° C.) 8.0 mm bottom parallel plate. The HyPPos were equilibriated at 50° C. for 15 min and then cooled to 25° C. for the experiments.

For the coacervate dense phases, 25.0 mm, 0.04 rad cone plate was used at top to minimize the error due to low viscosity values. The samples were loaded to a custom made 30.0 mm (diameter)×5 mm (height) closed cup to minimize the evaporation of water.

Adhesion Measurements

Lapshear Adhesion Test

The lapshear strength measurements were carried out by following ASTM D1002 with minor modifications. For the lapshear measurement, microscope glass slides from VWR were used. The substrates were cleaned by sonicating it in hexane, acetone, and ethanol. The dried substrates were then further oxidized by Piranha treatment. Afterwards, the substrates were thoroughly cleaned with DI water and dried at 110° C. The dry substrates were then exposed to 5 min air plasma treatment prior to use. The substrates were immersed in water and the coacervate dense phase (40 μL on each surface) was deposited to the marked area (3.2 cm2). The coacervate was allowed to spread on surfaces underwater for 5 min. Afterwards, two substrates were joined and left underwater till the joined area was then exposed to UV-A irradiation (λ=320-420 nm, intensity at substrate=150 mW/cm2) for initiating the cross-linking reaction for 10 min underwater. To demonstrate the robustness of underwater adhesion by HyPPos, prior to the force measurements, the substrates were remained immersed underwater for 12 h. The wet substrates were quickly attached to the clamps using a sand paper and the sheared at a rate of 1.3 mm/min. The force values were recorded (FIG. 7) and the lapshear strength was calculated from the following equation.

Lapshear strength=(Maximum force load)/(Lap joint area)

Figure 7:
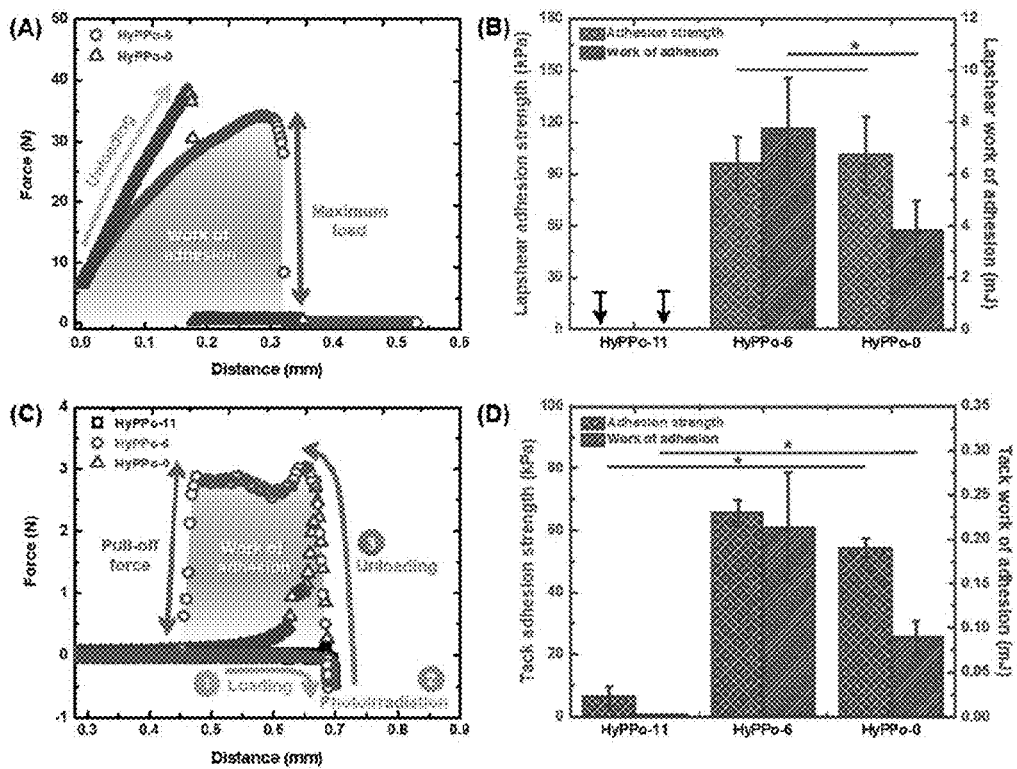
FIG. 7A is a graphical representation of representative force curves of HyPPo-6 and HyPPo-0 during the unloading of lapshear adhesion measurements.
FIG. 7B is a graphical representation of lapshear adhesion strength and work of adhesion quantified from the force curves of FIG. 7A.
FIG. 7C is a graphical representation of representative force curves of HyPPo-11, HyPPo-6, and HyPPo-O during tack adhesion measurements.
FIG. 7D is a graphical reprersenation of tack adhesion strength and work of adhesion quantified from the force curves of FIG. 7C. All the measurements shown in FIGS. 7A-7D were performed underwater and repeated at least five times. The data represented in the bar diagrams are in terms of mean±standard deviation, and '*' represents the statistical significance among the samples using a Tukey mean comparison test (p<0.05).

The lapshear work of adhesion was calculated from the are under the force-distance curve (FIG. 7). For each HyPPo dense phases, the experiment was repeated for at least five times.

Tack Adhesion Test

The tack adhesion test was performed using a custom-built adapter for the texture analyzer. First, the coacervate dense phases (40 μL) were loaded on to microscope slides (cleaned similarly as lapshear test substrates) sandwiched between plexiglass underwater. The top segment of the plexiglass has holes (12 mm diameter) through which underwater contact can be made with the dense phase. After allowing the coacervate to spread for 10 min, the force sensor arm of the texture analyzer equipped with UV-A LED (λ=340-355 nm, intensity at substrate=50 mW/cm2) and quartz light guide was brought in contact to the dense phase (FIG. 7). The deposited layer of coacervates were loaded to −0.5 N. Once the determined preload (−0.5 N) was reached, the UV-A LED was started and photoirradiated the dense phases under the preload for 10 min. The force arm was then retracted at a rate of 5 mm/min and the maximum load value was recorded as the pull-off force (FIG. 7) and the tack adhesion strength was calculated from the following equation.

Tack adhesion strength=(Pull-off force)/(Area of contact)

The tack work of adhesion was calculated from the area under the force-distance curve (FIG. 7). For each HyPPo dense phases, the experiment was repeated for at least seven times.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A non-ionic polymer coacervate represented by Formula I:

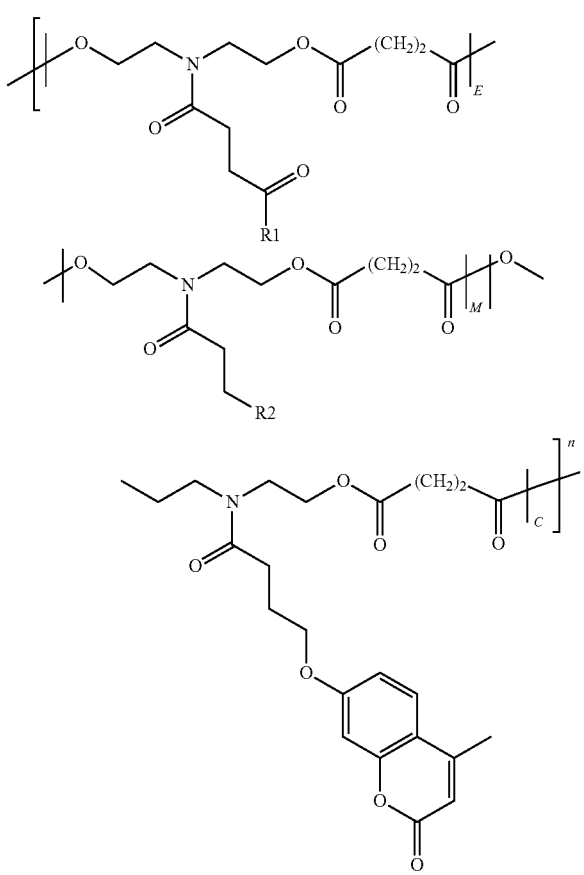

where R1 is selected from moieties that include an N- or N,N-substituted secondary or tertiary amide, R2 is selected from aliphatic groups, unsubstituted aromatic functional groups, and aromatic groups functionalized with one or more hydroxyl groups, n is from about 10 to about 500, E is from about 60 to about 95, M is from 0 to about 40, C is from about 5 to about 40, and where the sum of M+E+C is 100.

2. The polymer of claim 1, where R1 is selected from 2-ethoxyethan-1-amine, Morpholine, bis(2-methoxyethyl) amine, and 2-methoxyethan-1-amine groups.

3. The polymer of claim 1, where R2 is selected from methyl, benzene, phenol, catechol, resorcinol and pyrogallol groups.

4. The polymer of claim 1, where the polymer is characterized by a molecular weight of from about 5 to about 200 kDa.

5. The polymer of claim 1, where the polymer has a lower critical solution temperature in aqueous medium of from about −20 to about 100° C.

6. An underwater adhesive composition that is prepared by crosslinking the polymer of claim 1.

7. A coacervate adhesive composition comprising a polymer having the formula

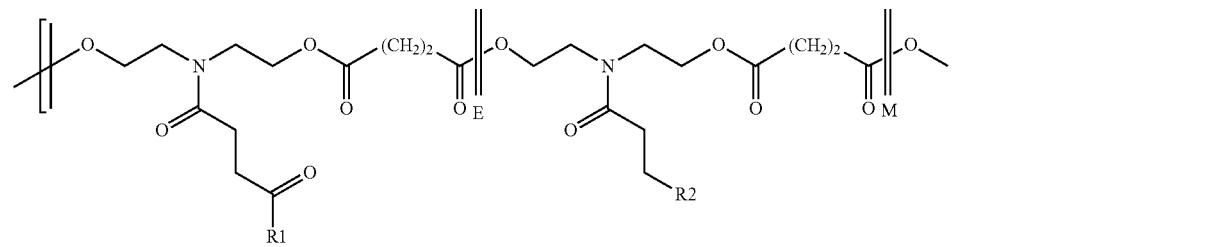

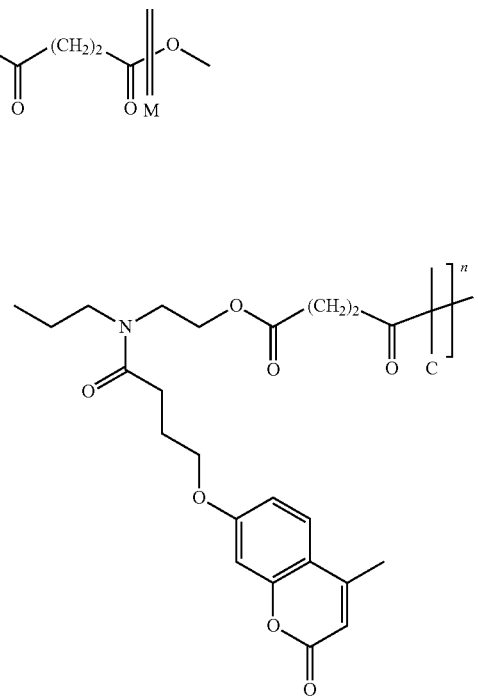

where R1 is selected from moieties that include an N- or N,N-substituted secondary or tertiary amide, R2 is selected from aliphatic groups, unsubstituted aromatic functional groups, and aromatic groups functionalized with one or more hydroxyl groups, n is from about 10 to about 500, E is from about 60 to about 95, M is from 0 to about 40, C is from about 5 to about 40, and where the sum of M+E+C is 100.

8. A method for adhering surfaces under wet conditions, the method comprising:
   contacting the surfaces with an adhesive composition comprising a polymer represented by the formula

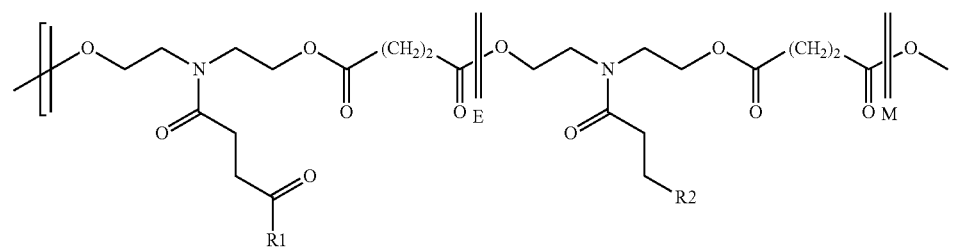

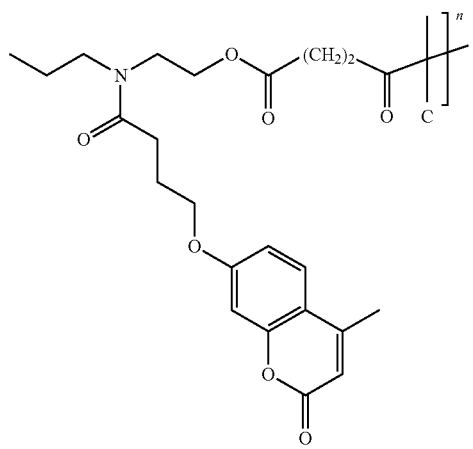

where R1 is selected from moieties that include an N- or N,N-substituted secondary or tertiary amide, R2 is selected from aliphatic groups, unsubstituted aromatic functional groups, and aromatic groups functionalized with one or more hydroxyl groups, n is from about 10 to about 500, E is from about 60 to about 95, M is from 0 to about 40, C is from about 5 to about 40, and where the sum of M+E+C is 100; and crosslinking the polymer to form an adhesive bond between the surfaces.

9. The method of claim 8, wherein the step of crosslinking includes exposing the polymer to UV radiation.

10. The method of claim 8, wherein the surfaces are underwater.

11. The method of claim 8, wherein at least one of the surfaces is biological tissue.

12. The method of claim 8, wherein step of contacting the surfaces occurs at a pH of from about 3 to about 9.

13. The method of claim 8, wherein step of contacting the surfaces occurs at an ionic strength that corresponds to from 0 to about 1 M NaCl.

14. The method of claim 8, where the step of crosslinking the polymer to form an adhesive bond occurs within about 1 hour or less.

15. The polymer of claim 1, wherein the sum of M+C is greater than or equal to 20.

* * * * *